United States Patent
Rivedal

(10) Patent No.: US 10,978,186 B2
(45) Date of Patent: Apr. 13, 2021

(54) PERSONALIZED WEARABLE PATIENT IDENTIFIERS THAT INCLUDE CLINICAL NOTIFICATIONS

(71) Applicant: Eric Rivedal, Denver, CO (US)

(72) Inventor: Eric Rivedal, Denver, CO (US)

(73) Assignee: Ricoh Company, Ltd., Tokyo (JP)

( * ) Notice: Subject to any disclaimer, the term of this patent is extended or adjusted under 35 U.S.C. 154(b) by 879 days.

(21) Appl. No.: 15/451,677

(22) Filed: Mar. 7, 2017

(65) Prior Publication Data

US 2018/0260525 A1    Sep. 13, 2018

(51) Int. Cl.
  *G16H 10/60* (2018.01)
  *G16H 40/20* (2018.01)
  *G16H 40/63* (2018.01)

(52) U.S. Cl.
  CPC .......... *G16H 10/60* (2018.01); *G16H 40/20* (2018.01); *G16H 40/63* (2018.01)

(58) Field of Classification Search
  CPC ......... G16H 10/60; G16H 40/20; G16H 40/63
  See application file for complete search history.

(56) References Cited

U.S. PATENT DOCUMENTS

| | | |
|---|---|---|
| 7,188,764 B2 | 3/2007 | Penuela |
| 7,386,949 B2 | 6/2008 | Riley |
| 7,481,370 B2 | 1/2009 | Davis et al. |
| 7,763,344 B2 | 7/2010 | Riley et al. |
| 7,779,569 B2 | 8/2010 | Riley et al. |
| 8,028,450 B2 | 10/2011 | Landsman et al. |
| 8,091,261 B2 | 1/2012 | Chadwick |
| 8,776,417 B2 | 7/2014 | Jain et al. |
| 2004/0237366 A1 | 12/2004 | Chadwick et al. |
| 2005/0040226 A1 | 2/2005 | Al-Sheikh |
| 2005/0055244 A1* | 3/2005 | Mullan ............ G16H 40/63 705/2 |
| 2005/0091896 A1 | 5/2005 | Kotik et al. |
| 2006/0149416 A1 | 7/2006 | Mohapatra et al. |

(Continued)

OTHER PUBLICATIONS

EndurID; IDMX Identification Management Express; www.endurid.com.

(Continued)

*Primary Examiner* — Fonya M Long
*Assistant Examiner* — Anthony Michael Balaj
(74) *Attorney, Agent, or Firm* — Duft & Bornsen, PC

(57) ABSTRACT

Systems and methods are provided for wearable patient identifiers. One embodiment is a labeling system that includes an interface, a memory storing rules that indicate on a patient-by-patient basis whether to print clinical notifications onto wearable patient identifiers, based on fields of electronic health records acquired via Health Level 7 (HL7) messaging, and a controller. The controller presents a Graphical User Interface (GUI) that includes interactive elements that enable alteration of the rules. The interactive elements include, for each rule: a first dialogue that indicates a field storing data to acquire from an electronic health record; a second dialogue that indicates a value to compare to the data; and an operator that logically combines the data and the value to arrive at a Boolean result. The controller determines whether to include a clinical notification in print data for a wearable patient identifier, based on the Boolean result.

20 Claims, 8 Drawing Sheets

(56) References Cited

U.S. PATENT DOCUMENTS

| | | | |
|---|---|---|---|
| 2006/0267753 A1 | 11/2006 | Hussey et al. | |
| 2007/0168223 A1 | 7/2007 | Fors et al. | |
| 2007/0243361 A1 | 10/2007 | Riley et al. | |
| 2007/0244922 A1* | 10/2007 | Draper | G06F 16/242 |
| 2008/0276504 A1 | 11/2008 | Cloninger | |
| 2011/0107637 A1 | 5/2011 | Bekker | |
| 2011/0202974 A1 | 8/2011 | Leader et al. | |
| 2012/0092693 A1 | 4/2012 | Jaudon et al. | |
| 2012/0224225 A1* | 9/2012 | Banfield | G06Q 10/10 |
| | | | 358/1.18 |
| 2013/0197932 A1* | 8/2013 | Herman | G16H 50/20 |
| | | | 705/2 |
| 2014/0240725 A1 | 8/2014 | Banfield et al. | |
| 2015/0096211 A1* | 4/2015 | Weinstein | G09F 3/02 |
| | | | 40/630 |
| 2016/0140307 A1 | 5/2016 | Brosnan et al. | |
| 2016/0188822 A1* | 6/2016 | Ryan | G16H 10/60 |
| | | | 705/3 |
| 2018/0002056 A1 | 1/2018 | Enos et al. | |

OTHER PUBLICATIONS

HL7 International; Health Level Seven International; Glossary of Terms; Ann Arbor, MI 2012.
http://endurid.com/product/healthcare/adult-wrist-bands/secure-wrist-band.
International Organization for Standardization; ISO Store Standards Catalogue; ISO/HL7 16527:2016.
International Organization for Standardization; ISO Store Standards catalogue; ISO/HL7 27932:2009.

* cited by examiner

US 10,978,186 B2

PERSONALIZED WEARABLE PATIENT IDENTIFIERS THAT INCLUDE CLINICAL NOTIFICATIONS

FIELD OF THE INVENTION

The disclosure relates to the field of health care, and in particular, to providing wearable patient identifiers.

BACKGROUND

It remains crucial that patients within a hospital are properly identified and treated by hospital personnel. If patients are improperly identified or if they are subject to clinical restrictions which are not clearly indicated to hospital personnel, then the patients may be at risk of injury or even death due to the lack of information. For example, if a patient is allergic to a specific medication, it is important to clearly indicate this to hospital staff in order to ensure that the patient is not exposed to that medication. For many conditions, it is not sufficient to simply update a chart for a patient with clinical notifications. Rather, the patient is also labeled with clinical restrictions (e.g., via one or more wristbands). This is especially important for patients who may travel to different areas of a hospital for treatment.

Present techniques for identifying and labeling patients utilize manual identification of each patient, manual detection of each clinical condition, and the printing (or handwriting, or pulling from stock) of a separate wrist band for each condition of the patient. This process is time-consuming, which hampers the speed of admissions into a hospital. It is also subject to human error, which increases the chances that incoming patients will be mislabeled resulting in mistreatment. Still further, for patients with multiple clinical restrictions, the use of multiple wristbands (one for each condition) may be cumbersome for both the patient and for hospital personnel.

Thus, hospitals continue to seek out enhanced techniques for increasing the speed of admissions, increasing the accuracy of patient labeling, and reducing the time required by hospital personnel to perform patient labeling.

SUMMARY

Embodiments described herein provide systems and methods for aggregating Health Level 7 (HL7) messaging for a patient from a variety of sources during admission of the patient into the hospital. The systems may, for example, analyze HL7 admissions, diagnoses, and other data to determine whether an incoming patient is subject to any clinical notifications (e.g., an allergy, a fall risk, etc.). These clinical notifications are identified for each patient based on customizable rules. The rules indicate values of HL7 data for a patient will trigger the placement of a clinical notification onto a wrist band for the patient. Multiple clinical notifications are integrated into a single wrist band, which ensures straightforward determination of clinical notifications for a patient by hospital personnel. Graphical User Interfaces (GUIs) may further be provided in order to enable customization of the rules.

One embodiment is a labeling system that includes an interface, a memory storing rules that indicate on a patient-by-patient basis whether to print clinical notifications onto wearable patient identifiers, based on fields of electronic health records acquired via Health Level 7 (HL7) messaging, and a controller. The controller presents a Graphical User Interface (GUI) that includes interactive elements that enable alteration of the rules. The interactive elements include, for each rule: a first dialogue that indicates a field storing data to acquire from an electronic health record; a second dialogue that indicates a value to compare to the data; and an operator that logically combines the data and the value to arrive at a Boolean result. The controller determines whether to include a clinical notification in print data for a wearable patient identifier, based on the Boolean result.

A further embodiment is a method that includes storing rules that indicate on a patient-by-patient basis whether to print clinical notifications onto wearable patient identifiers, based on fields of electronic health records acquired via Health Level 7 (HL7) messaging, and directing a display to present a Graphical User Interface (GUI) that includes interactive elements that enable alteration of the rules. The interactive elements comprise, for each rule: a first dialogue that indicates a field storing data to acquire from an electronic health record; a second dialogue that indicates a value to compare to the data; and an operator that logically combines the data and the value to arrive at a Boolean result. The method further includes determining whether to include a clinical notification in print data for a wearable patient identifier, based on the Boolean result.

A further embodiment is A non-transitory computer readable medium embodying programmed instructions which, when executed by a processor, are operable for performing a method. The method includes storing rules that indicate on a patient-by-patient basis whether to print clinical notifications onto wearable patient identifiers, based on fields of electronic health records acquired via Health Level 7 (HL7) messaging, and directing a display to present a Graphical User Interface (GUI) that includes interactive elements that enable alteration of the rules. The interactive elements comprise, for each rule: a first dialogue that indicates a field storing data to acquire from an electronic health record; a second dialogue that indicates a value to compare to the data; and an operator that logically combines the data and the value to arrive at a Boolean result. The method further includes determining whether to include a clinical notification in print data for a wearable patient identifier, based on the Boolean result.

Other exemplary embodiments (e.g., methods and computer-readable media relating to the foregoing embodiments) may be described below.

DESCRIPTION OF THE DRAWINGS

Some embodiments of the present invention are now described, by way of example only, and with reference to the accompanying drawings. The same reference number represents the same element or the same type of element on all drawings.

DETAILED DESCRIPTION

The figures and the following description illustrate specific exemplary embodiments of the invention. It will thus be appreciated that those skilled in the art will be able to devise various arrangements that, although not explicitly described or shown herein, embody the principles of the invention and are included within the scope of the invention. Furthermore, any examples described herein are intended to aid in understanding the principles of the invention, and are to be construed as being without limitation to such specifically recited examples and conditions. As a result, the invention is not limited to the specific embodiments or examples described below, but by the claims and their equivalents.

Figure 1:
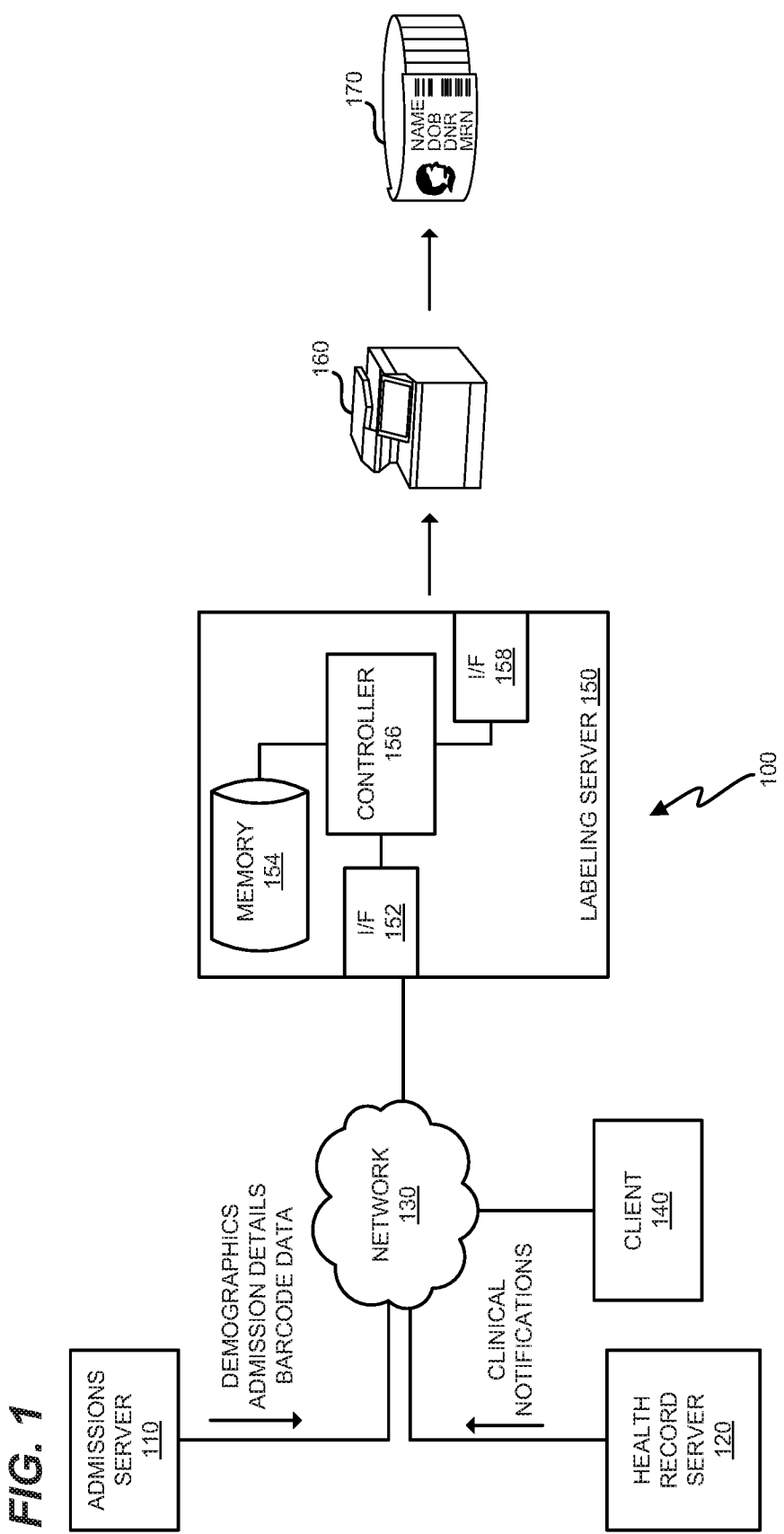
FIG. 1 is a diagram of an admissions environment in an exemplary embodiment.

FIG. 1 is a diagram of an admissions environment 100 in an exemplary embodiment. Admissions environment 100 comprises any suitable combination of systems, components, and/or devices that facilitate the admission of patients into a hospital. For example, admissions environment 100 may include one or more computers for use by hospital personnel in order to retrieve and/or update electronic health records for incoming patients based on Health Level 7 (HL7) messaging. Based on the electronic health records for a patient, admissions environment 100 generates a personalized wrist band 170 for that patient. The wrist band includes a list of clinical notifications that have been automatically determined to apply to the patient based on the health records of that patient.

In this embodiment, admissions environment 100 includes admissions server 110, health record server 120, and labeling server 150. Using admissions server 110, hospital personnel may update patient health records based on responses to intake questionnaires, results of intake vitals, etc. These updates may be provided to health record server 120 (which stores health records for patients) via messages that are formatted in accordance with HL7 standards and directed to health record server 120. Common information acquired by admissions server 110 may include patient photographs, patient demographics, barcode data for a unique number identifying the patient, and details regarding how the patient was initially admitted to the hospital (e.g., via an emergency room, in accordance with a scheduled appointment, etc.). HL7 messages from admissions server 110 may further be transmitted via network 130 for use by labeling server 150 as desired.

Health record server 120 stores clinical data, diagnoses, and other records for a patient in a database. Health record server 120 may transmit HL7 messages via network 130 for later processing by labeling server 150, and may be updated based on HL7 messaging from other entities within admissions environment 100.

After health records for an incoming patient have been created and/or updated at health record server 120, hospital personnel may desire to generate a personalized wearable patient identifier (e.g., wrist band) for the patient that automatically includes any relevant clinical notifications for the patient. To this end, one or more clients 140 may be utilized to direct labeling server 150 in printing a custom wrist band for the patient. Client 140 comprises any suitable terminal or device capable of interacting with labeling server 150 in order to provide commands or other user input. Client 140 may comprise, for example, a computer, tablet, mobile phone, etc.

In response to directions from client 140, labeling server 150 generates wrist bands that each uniquely indicate the identity of a patient, as well as any clinical notifications for that patient. In this embodiment, labeling server 150 utilizes network interface (I/F) 152, memory 154, controller 156, and printing I/F 158 to facilitate the printing of wrist bands. Controller 156 directs the operations of labeling server 150 in preparing customized wrist bands for patients based on electronic health records (e.g., carried by HL7 messaging transmitted over network 130). These wrist bands include personalized clinical notifications for patients that are automatically determined based on the electronic health records for those patients. Controller 156 may be implemented as custom circuitry, as a hardware processor executing programmed instructions, etc.

I/F 152 is utilized by controller 156 to acquire electronic health records for use by labeling server 150. In one embodiment, network I/F 152 passively awaits incoming HL7 messages provided by admissions server 110 and/or health record server 120. However, in further embodiments, controller 156 actively operates network I/F 152 to request electronic health records via network 130. In still further embodiments, network I/F 152 actively intercepts HL7 messaging between admissions server 110 and health record server 120 by monitoring network 130, and updates locally stored health records in memory 154 based on these intercepted messages. Controller 156 utilizes printing I/F 158 to communicate with printer 160. For example, controller 156 may use printing I/F 158 to transmit print data and commands to printer 160. Network I/F 152 and printing I/F 158 comprise any suitable interfaces capable of exchanging data via wired or wireless means to other electronic devices. For example, network I/F 152 and printing I/F 158 may comprise Ethernet interfaces, interfaces compliant with IEEE 802.11 standards, etc.

Memory 154 stores rules which are utilized by controller 156 to automatically determine whether or not to include clinical notifications on wrist bands for each incoming patient based on the electronic health records of those patients. When controller 156 determines that a clinical notification should be included on a wrist band for a patient, controller 156 updates print data for the wrist band to include the clinical notification. This process of analyzing an electronic health record based on a rule, determining whether to include a clinical notification, and updating print data for a wrist band may be performed multiple times (e.g., once per rule) until finalized print data for the wrist band (e.g., including multiple clinical notifications) has been generated.

Printer 160 receives print data from labeling server 150 and prints wrist bands based on the print data. Printer 160 may receive the print data as Page Description Language (PDL) print data or as a bitmap. If the print data is received as PDL, printer 160 may rasterize the print data before printing. Printer 160 may further utilize custom print media that include a pre-cut wrist band which is peelable from a vinyl backing. For example, different types of custom print media may include differently sized wrist bands for wrists of varying sizes. After printing, wrist band 170 is placed onto an incoming patient to uniquely identify the patient, as well as any relevant clinical notifications for the patient. The patient may then enter the hospital with the assurance that hospital personnel will use wrist band 170 to quickly identify any relevant clinical notifications and adjust treatment of the patient accordingly.

The particular arrangement, number, and configuration of components described herein is exemplary and non-limiting. Illustrative details of the operation of admissions environment 100 will be discussed with regard to FIG. 2. Assume, for this embodiment, that a patient is being checked in, and that a nurse is utilizing admissions server 110 to input data describing the patient. The nurse proceeds to assign a unique identification number to the patient, and generates one or more electronic health records based on patient responses to a questionnaire. These electronic health records are then transmitted from admissions server 110 to health record server 120 via HL7 messaging.

Figure 2:
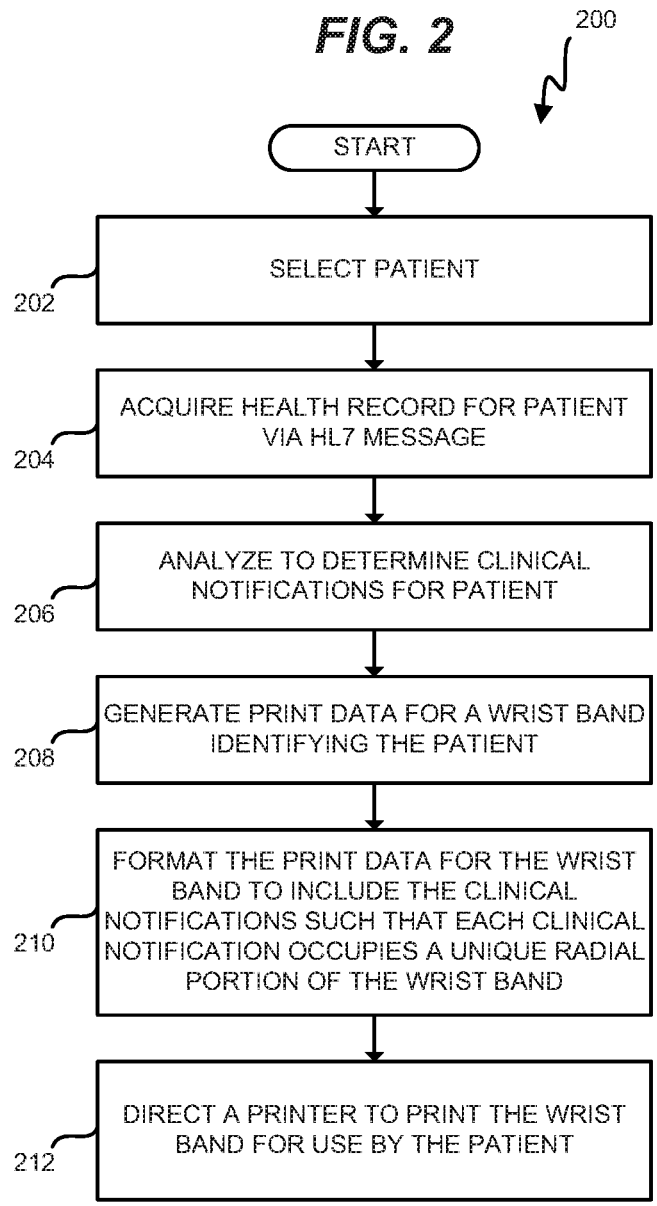
FIG. 2 is a flowchart illustrating a method for utilizing HL7 data to print a wrist band that includes multiple clinical notifications in an exemplary embodiment.

FIG. 2 is a flowchart illustrating a method 200 for utilizing HL7 data to print a wrist band that includes multiple clinical notifications in an exemplary embodiment. The steps of method 200 are described with reference to admissions environment 100 of FIG. 1, but those skilled in the art will appreciate that method 200 may be performed in other medical environments as desired. The steps of the flowcharts described herein are not all inclusive and may include other steps not shown. The steps described herein may also be performed in an alternative order.

After the admissions server 110 has been used to generate and/or update electronic health records for the patient, the patient is almost ready for admission to the hospital. However, the patient herself has not yet been provided with any wearable patient identifier (e.g., wristband), and also has not been labeled with any specific clinical notifications. This means that the patient would be at risk of improper medical treatment if he or she entered the hospital at this point in time. To this end, a nurse operates client 140 in order to facilitate generation of a personalized wrist band. The personalized wrist band will identify the patient and provide clinical notifications for the patient.

The patient is selected, for example, via client 140 by selecting a unique ID for the patient (step 202). This unique ID may have been assigned by admissions server 110 or may already be indicated in existing health records of the patient. The unique ID uniquely identifies the patient from other patients in the hospital, and may comprise a Medical Record Number (MRN), a Social Security Number (SSN), or a combination of these. In one embodiment, controller 156 acquires personal identifying information for the patient from an HL7 admissions message.

Controller 156 acquires one or more electronic health records for the patient via HL7 messages (step 204). This process may involve actively querying admissions server 110 or health records server 120 in order to acquire HL7 messages having health record data that corresponds with the unique ID (or other personal identifying information). For example, controller 156 may provide an HL7 query to admissions server 110 and/or health records server 120 in order to request HL7 messages that include electronic health records associated with the MRN or SSN of the patient. In further embodiments where labeling server 150 monitors HL7 messaging to update internally stored health records for patients in memory 154, controller 156 acquires the electronic health records from memory 154.

With one or more electronic health records acquired for the patient, controller 156 analyzes the electronic health records to determine clinical notifications for the patient (step 206). As used herein, a clinical notification is a label which indicates that the patient should receive different medical treatment than provided by default at the hospital, and is based on the medical condition and/or health of the patient. Thus, a patient desiring access to cable television would not be subject to a clinical notification, because there is no change to medical treatment nor is this desire indicative of a medical condition of the patient. Clinical notifications are described in detail below, but may include allergies, increased fall risk, dietary restrictions, etc. The process of utilizing rules to automatically determine whether to include clinical notifications on a patient wrist band are described in detail with regard to method 300 of FIG. 3 below.

Having analyzed the electronic health records for the patient and determined which notifications for the patient should be indicated on a wrist band for the patient, controller 156 generates print data for the wrist band identifying the patient (step 208). The print data uniquely identifies the patient from other patients, for example based on a picture of the patient and/or barcode included in the print data. Controller 156 further formats the print data for the wrist band to include the clinical notifications for the patient, such that each clinical notification occupies a unique (e.g., non-overlapping) radial portion of the wrist band as worn (step 210). Furthermore, controller 156 may ensure that the print data for each clinical notification results in a corresponding radial section of wrist band 170 having a unique color. Controller 156 may generate the print data as PDL, such as Portable Document Format (PDF) or Advanced Function Printing (AFP). Alternatively, controller 156 may generate the print data in a raw format such as a bitmap. Controller 156 may also store the print data in memory 154 in order to facilitate rapid re-printing of the wrist band in the case that the wrist band is lost or destroyed.

Controller 156 operates I/F 158 to direct printer 160 to print the wrist band for use by the patient (step 212). For example, controller 156 may transmit the print data to printer 160 as a print job for printing. Printer 160 proceeds to print onto custom print media for the wrist band, resulting in a customized wrist band for the patient. The patient may then wear the wrist band in order to ensure that hospital personnel correctly identify any relevant clinical notifications.

Figure 3:
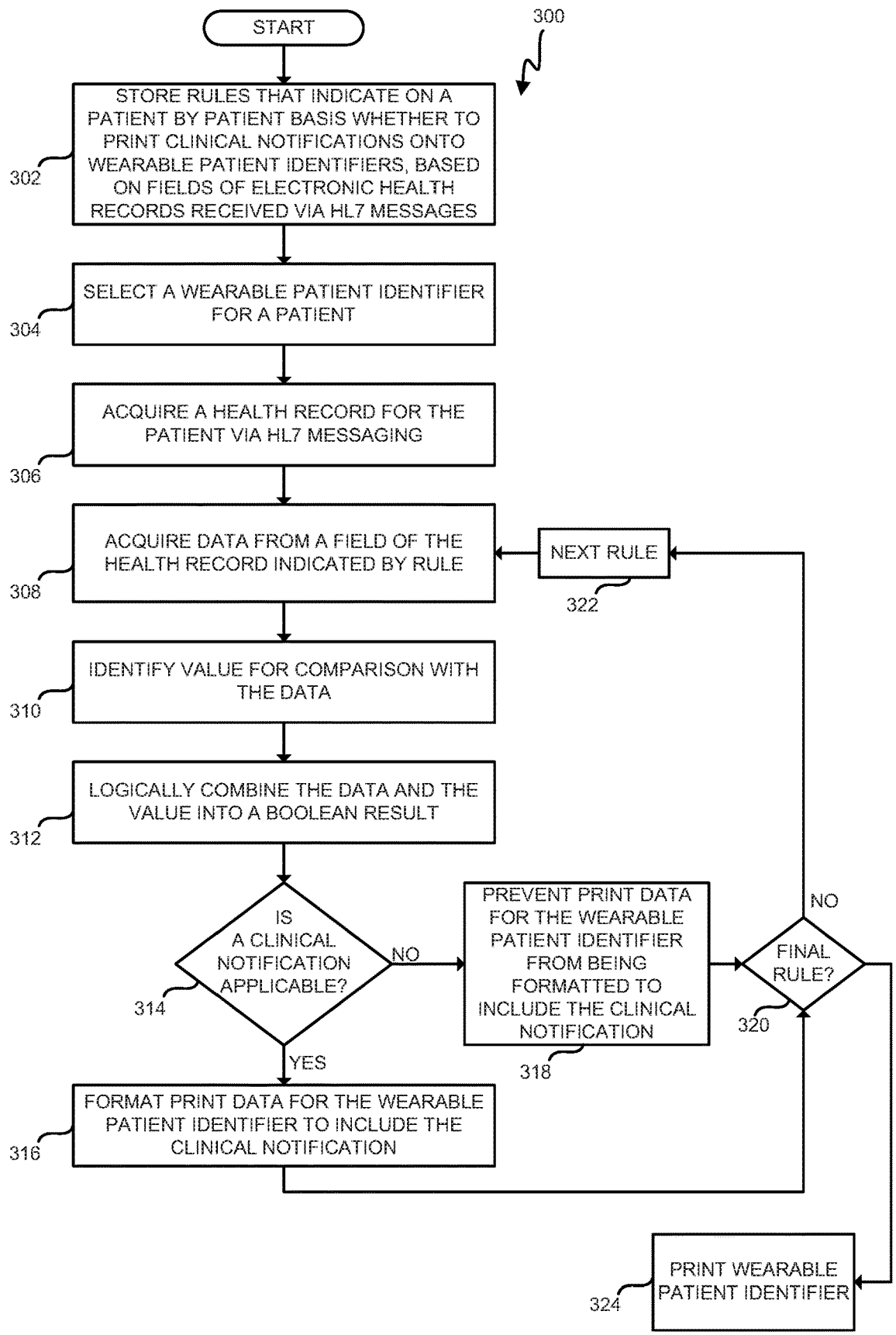
FIG. 3 is a flowchart illustrating a method for automatically determining clinical notifications to apply to a wearable patient identifier in an exemplary embodiment.

FIG. 3 provides further details of the operation of rules which indicate whether to include clinical notifications on wearable patient identifiers. FIG. 3 is a flowchart illustrating a method 300 for automatically determining clinical notifications to apply to a wearable patient identifier (e.g., a wrist band) in an exemplary embodiment. According to FIG. 3, memory 154 stores rules that indicate on a patient-by-patient basis whether to print clinical notifications onto wearable patient identifiers (step 302). Controller 156 selects a wearable patient identifier for a patient (step 304). For example, a user may enter an MRN for a patient that requires a new wearable patient identifier. Controller 156 further acquires at least one electronic health record for that patient via HL7 messaging (step 306). The electronic health record(s) may be acquired by querying health record server 120 with an HL7 request based on the MRN, or by any methods already discussed above.

Next, controller 156 analyzes the acquired electronic health records based on the rules to determine whether any clinical notifications will be printed onto the wearable patient identifier. Each rule provides one or more logical conditions which indicate whether or not a specific clinical notification is applicable to a patient. As used herein, a "logical condition" is a comparison from which a Boolean result may be acquired. Thus, a rule for "fall risk" might include multiple logical conditions (e.g., one logical condition checking for a diagnosis of "dementia," another logical condition checking for a medical order of "fall risk," etc.) which are combined via logical AND or logical OR operators.

Rules are defined globally, but the outcome of each rule is determined individually for each patient. That is, the same rules will be used to determine which clinical notifications apply to each patient, but the outcome of each rule will vary depending on the contents of electronic health records for the specific patient being considered.

Each rule indicates at least one field (e.g., an Extensible Markup Language (XML) field or a character ("|") delimited field) from which to acquire data within electronic health records (e.g., as stored within memory 154 in response to HL7 messaging). For example, a rule may indicate a field based on a name of the field, such as "administrativeGenderCode" (a field that designates the gender of a patient). A rule may further indicate a desired field based on the name of a parent field in which the desired field is nested. These field names may, for example, correspond with fields defined by HL7 messaging standards.

Controller 156 performs its analysis by selecting a rule, and acquiring data from a field indicated by the rule (within the electronic health records for the patient) that is indicated by the rule (step 308). Thus, controller 156 may search each electronic record of the patient for a field indicated by a rule, and extract data from within that field.

Rules that define multiple logical conditions may indicate that data should be acquired from multiple fields that have different names. In these circumstances, controller 156 acquires data from each field indicated by the rule. In certain cases, a rule may indicate just one field by name, yet controller 156 may detect multiple fields having that name. In these cases, controller 156 may acquire data from each of those fields, acquire data from one specific field (e.g., data from the field that was most recently updated/created), or provide an error report to a user requesting that the user select a field from which to acquire the data.

Controller 156 further identifies a value for comparison with the data extracted from the health records (step 310). This value may be stored in memory 154, and provides a basis for comparing the data. For example, the value may be a threshold level of blood pressure associated with hypertension, may be a wildcard character which determines whether any data exists for a given field, etc. At least one value may be identified for each piece of data acquired in step 308. Controller 156 logically combines the data and the value into a Boolean result (step 312). For example, controller 156 may determine whether the data is greater than the value, less than the value, equal to the value, etc., in order to arrive at a conclusion of TRUE or FALSE. In cases where no field indicated by a rule exists in the electronic health records, controller 156 may infer a Boolean result of FALSE without comparing the retrieved data to a value.

If a rule provides multiple logical conditions (e.g., a blood pressure higher than a first value and a cholesterol level above a second value), then controller 156 may combine the Boolean results for each logical condition via logical operators (e.g., as indicated by the rule) in order to achieve a final Boolean result. This final Boolean result determines whether the clinical notification for the rule is applicable to the patient or not.

Based on the Boolean result, controller 156 determines if the clinical notification for the current rule is applicable to the patient (step 314). If the clinical notification is applicable to the patient, then controller 156 formats print data for the wearable patient identifier to include the clinical notification (step 316). Alternatively, if the clinical notification is not applicable to the patient, then controller 156 prevents print data for the wearable patient identifier from being formatted to include the clinical notification (step 318). Controller 156 determines whether the last rule has been considered (step 320). If other rules remain for analysis (step 320), controller proceeds to select a next rule (step 322). Alternatively, if no further rules remain for analysis, controller 156 directs printer 160 to print the wearable patient identifier (step 324). In further embodiments, the electronic health records may be reviewed for compliance with multiple rules at once in parallel.

FIG. 3 provides a substantial benefit over prior techniques for generating wrist bands and other wearable patient identifiers, because it harnesses information in electronic health records to automatically determine what clinical notifications (if any) to include on wrist bands, on an individualized basis and without the need for user intervention.

Figure 4:
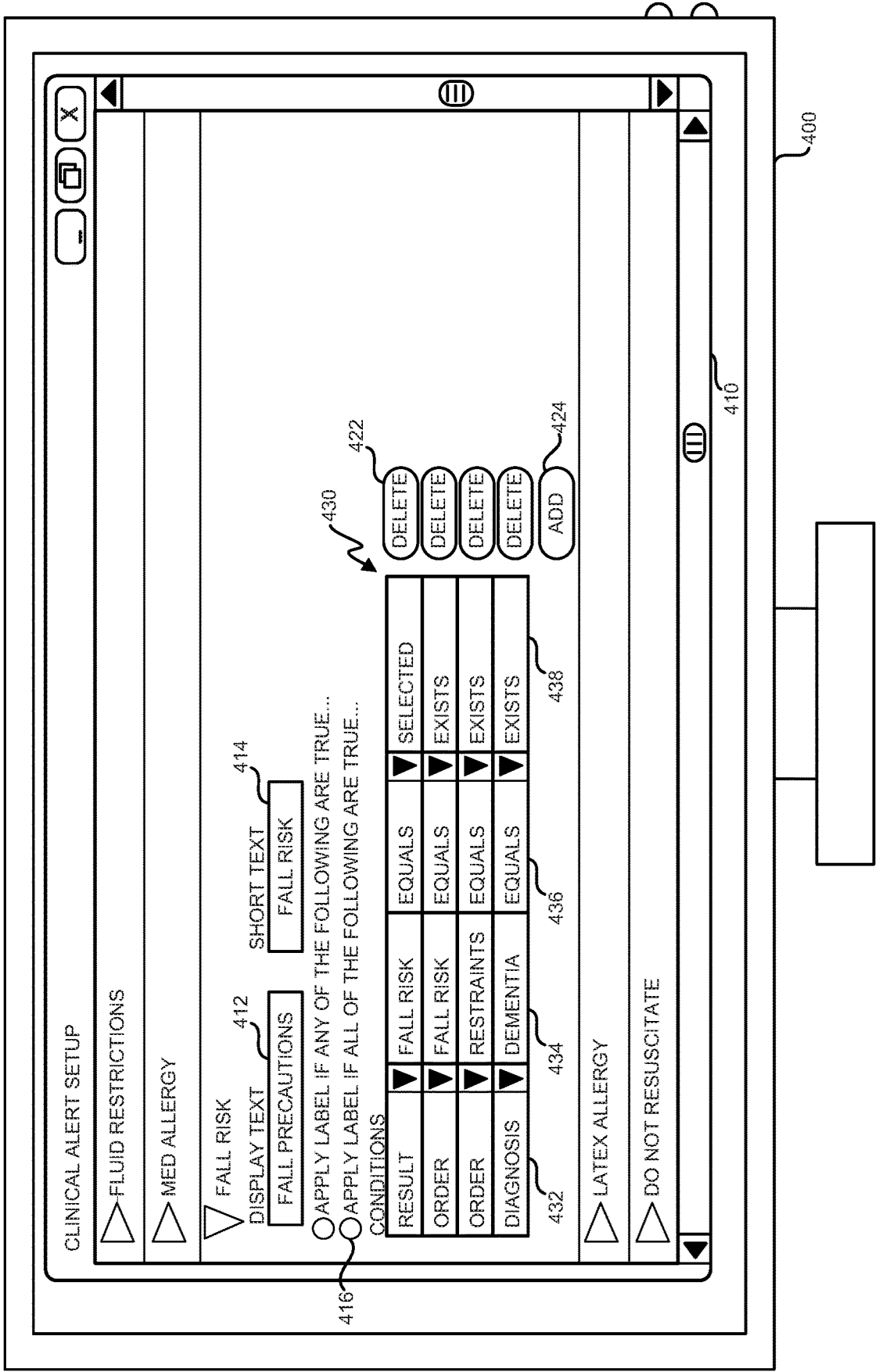
FIG. 4 is a diagram illustrating a GUI for customizing clinical notification rules in an exemplary embodiment.

FIG. 4 illustrates a GUI which may be utilized by labeling server 150 and/or client 140 in order to modify rules stored in memory 154. Specifically, FIG. 4 is a diagram illustrating a GUI 410 for customizing rules in an exemplary embodiment. GUI 410 is presented via display 400 (e.g., a monitor). In this embodiment, GUI 410 includes rules that each indicate whether to include a different clinical notification on a wrist band. The clinical notifications include fluid restrictions, medical allergies, fall risks, latex allergies, and do not resuscitate directives.

Interactive elements for altering the fall risk rule are shown in detail with respect to FIG. 4. For example, text field 412 and text field 414 are interactive elements that provide alternative textual descriptions that may be printed onto a wrist band for the fall risk clinical notification. These text fields are editable by a user, and changes to these text fields may alter how the fall risk clinical notification appears when included on a wrist band.

Section 430 of GUI 410 provides interactive elements that define various conditions for the fall risk rule. Specifically, each condition is defined by a row of section 430. Each row comprises a dialogue 432, a dialogue 434, a dialogue 436, and a dialogue 438. Dialogue 432 (e.g., a drop-down menu) and dialogue 434 (e.g., an editable text field) in combination indicate a field of an electronic health record for retrieving data. The field may be an XML, field or a character (e.g., "pipe", "forward slash" or other character) delimited field, and the field may be identified by name. In one embodiment, the name provided for the field corresponds with a field name defined in HL7 standards. Dialogue 438 (e.g., an editable field) provides a value, and dialogue 436 (e.g., a drop-down menu) provides a logical operator that enables comparison of the value to data retrieved from the field in order to yield a Boolean result. Buttons 422 enable the deletion of individual conditions of the fall risk rule, and button 424 enables the creation of a new condition for the fall risk rule. Meanwhile, radio buttons 416 indicate how Boolean results for individual conditions are to be logically combined in order to arrive at a final Boolean result indicating whether or not to include a clinical notification for fall risk onto the wrist band of a patient. Specifically, one radio button unites conditions via logical OR operators, and the other radio button unites conditions via logical AND operators. Controller 156 detects modifications to the dialogues and other interactive elements, and updates the rules stored in memory 154 based on the modifications.

While FIG. 4 illustrates a GUI utilized to activate/trigger the application of clinical notifications for a wristband, a similar GUI, including similar features, may be utilized in order to logically define rules for deactivating clinical notifications (i.e., to remove print data for a clinical notification from a wrist band that currently includes the clinical notification).

Figure 5:
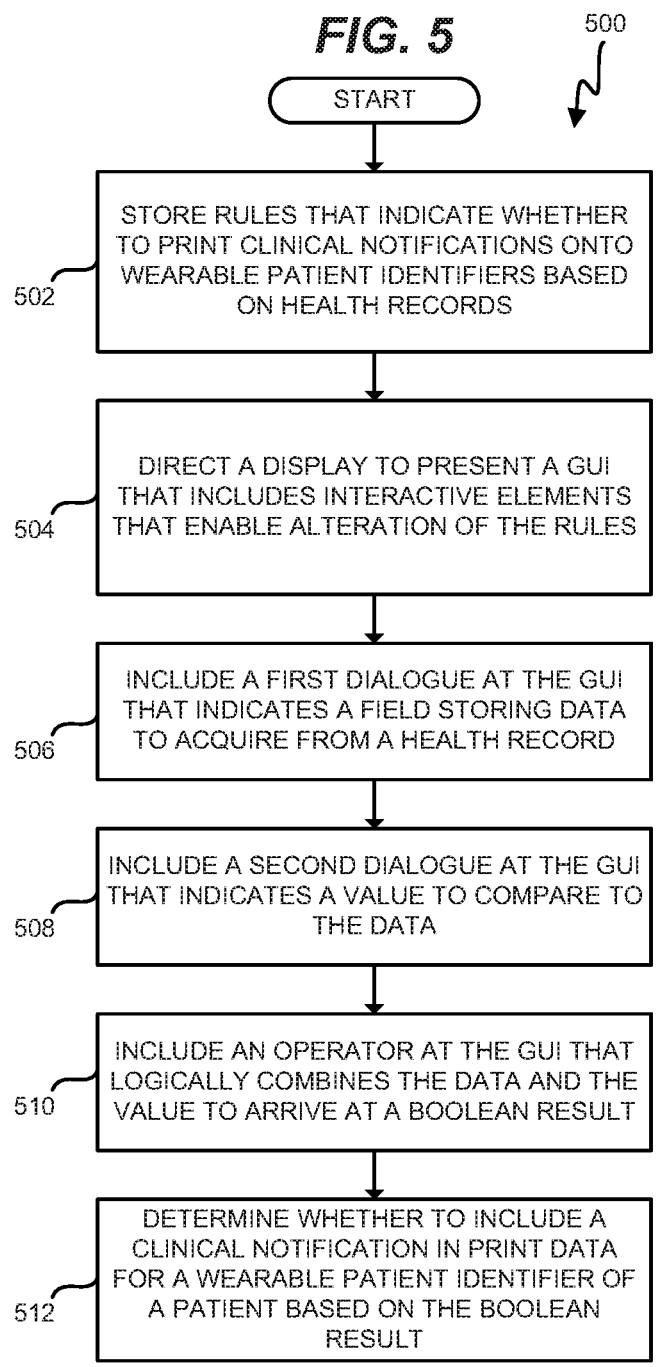
FIG. 5 is a flowchart illustrating a method for presenting a GUI that edits rules for wearable patient identifiers in an exemplary embodiment.

FIG. 5 is a flowchart illustrating a method for presenting a GUI 410 that edits rules for wearable patient identifiers in an exemplary embodiment. According to method 500, memory 154 stores rules that indicate whether to print clinical notifications onto wearable patient identifiers based on electronic health records received via HL7 messaging (step 502). Controller 156, upon receiving user input from client 140 indicating that a user desires to view or revise the rules, directs display 400 to present GUI 410 (step 504). GUI 410 includes interactive elements that enable alteration of the rules.

Specifically, controller 156 includes a first dialogue 434 at GUI 410 that indicates a field storing data to acquire from an electronic health record (step 506). For example, dialogue 434 may indicate the name of a field expected to be found within electronic records for incoming patients. Controller 156 further includes a second dialogue 438 at GUI 410 that indicates a value to compare to the data (step 508), and an operator at the GUI (defined by dialogue 436) that logically combines the data and the value to arrive at a Boolean result (step 510). Based on the Boolean result, controller 156 determines whether to include a clinical notification in print data for a wearable patient identifier of a patient (step 512).

Figure 6:
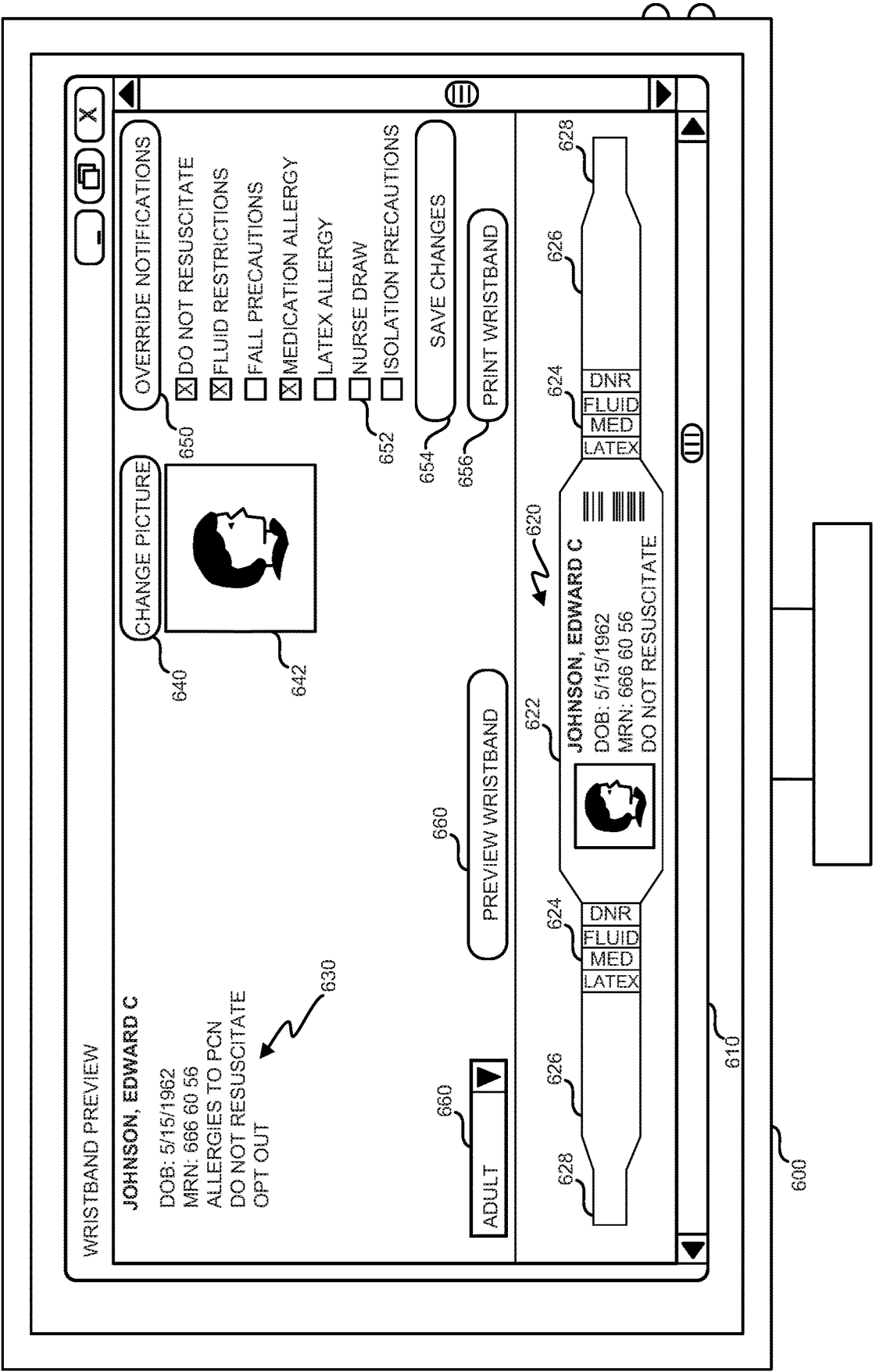
FIG. 6 is a diagram illustrating a GUI for customizing a wristband indicating multiple clinical notifications in an exemplary embodiment.

GUIs may be utilized not just to modify rules, but also to control how individual wrist bands are printed. For example, FIG. 6 is a diagram illustrating a GUI 610 for customizing a wristband having multiple clinical notifications in an exemplary embodiment. GUI 610 is presented via display 600, and may be presented just before printing a wrist band for a patient, in order to ensure that the wrist band includes any desired clinical notifications and personal information. A print preview 620 is included at GUI 610, and print preview 620 illustrates a wide segment 622 of a wrist band displaying personal information, a middle segment 624 displaying clinical notifications in unique radial portions of the wrist band, and an unprinted narrow segment 628 (e.g., for holding an adhesive enabling securement of the wrist band). Different locations along the length of print preview 620 will correspond with different radial portions of the printed wrist band as worn.

GUI 610 further includes patient personal information 630, button 640 for changing a picture 642 of the patient, and button 650, which enables automatically determined clinical notifications for a specific wrist band to be overridden manually via check boxes 652. In cases where clinical notifications are overridden, controller 156 may direct GUI 610 to display a warning message asking for the user to confirm overriding the clinical notifications. Button 654 saves changes to clinical notifications in memory 154, and button 656 prints the wrist band for use by the patient. Button 660 enables the print preview to be generated or refreshed, while drop-down menu 670 enables a user to select from between multiple different wrist sizes. Each wrist size corresponds with a different custom print media having a differently sized wrist band. To account for these changes in wrist band size, controller 156 may update print data for the wrist band (e.g., by changing a size or location of print data) in order to accommodate the change in size.

Figure 7:
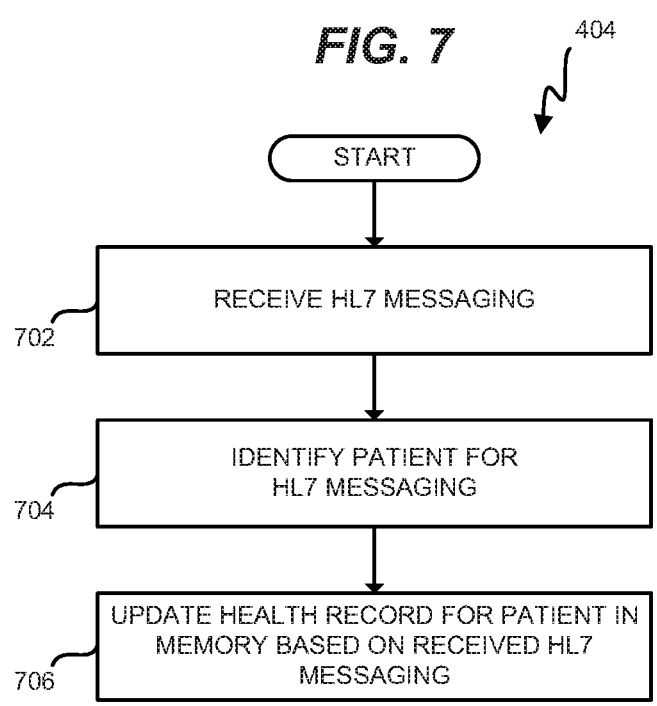
FIG. 7 is a flowchart illustrating a method for updating patient health records based on HL7 messages in an exemplary embodiment.

In further embodiments, it may be desirable to increase the speed at which print data is generated for wrist bands. This may be achieved by enhancing the speed at which health records are reviewed for clinical notifications. To this end, a locally stored copy of patient health records may be kept in memory 154. Controller 156 may then dynamically update electronic health records stored in memory 154 based on received HL7 messaging. FIG. 7 is a flowchart illustrating a method 700 for updating patient health records based on HL7 messages in an exemplary embodiment. Controller 156 of labeling server 150 receives HL7 messaging (step 702). This may be performed, for example, by directly receiving new HL7 messages, or acquiring communications between other servers that are exchanging HL7 messaging. For each HL7 message, controller 156 identifies a patient corresponding to the message (e.g., based on an MRN within the message, or an encounter number indicating a unique person and episode of care) (step 704). Controller 156 then proceeds to update a health record for the patient stored in memory 154, based on the contents of the HL7 message (step 706). For example, controller 156 may update individual fields of a health record in order to match updated fields provided in the HL7 messaging. In a further example, an HL7 A01 admissions message may be sent out via network 130 network and received by labeling server 150, which updates health records in memory 154 to indicate a new admission of a patient. Health record sever 120, and other entities within network 130 (e.g., a radiology system, a cardiology system, an emergency department system, etc.), may perform similar update operations.

EXAMPLES

In the following examples, additional processes, systems, and methods are described in the context of an admissions system that generates personalized wrist bands for patients.

In this example, a variety of types of clinical and admissions are reviewed in order to determine whether to include a clinical notification on a wrist band of a patient. For example, if electronic health records indicate a diagnosis of renal failure, the patient is provided a clinical notification of "FLUID RESTRICTIONS." Further examples include detection of a prior fall incident leading to a "FALL RISK" notification, a combination of patient age greater than sixty and use of an assistive device for walking leading to a "FALL RISK" notification, detection of any allergy to medication resulting in a "MED ALLERGY" notification, detection of a diagnosis of a latex allergy leading to a "LATEX" notification, detection of a patient Opt Out leading to an "OPT OUT" notification, charting of any multi-lumen vascular access device insertion leading to a "NURSE DRAW" notification, detection of an advance directive set to "Do Not Resuscitate" leading to a "DNR" notification, and detecting orders for any diet other than "regular" leading to a "SPECIAL DIET" notification.

The following paragraphs describe classes of data that may be harvested from electronic health records for patients. A first class of data is known as "results." This category includes any type of result that comes from data entry or that is captured by an Electronic Health Record (EHR). Examples of results are blood pressure, pulse, potassium, and MRSA+. This class of information benefits from the use of a numerical comparison value in order to check for a clinical notification. For example, blood pressure may be compared against predefined numerical values in order to check for hypertension. Results may be harvested from HL7 ORU messages.

A second class of data is known as "orders." This category includes orderable methods of patient care (herein also referred to as "computerized provider order entry" (CPOE)). Orders will generally be either active or inactive. Once an order is discontinued, the associated clinical notification is removed/deactivated. Examples of orders are fluid restrictions, nurse draw, and fall precautions. This class of information benefits from the use of a named comparison value in order to check for a named clinical notification. Orders may be harvested from HL7 ORM messaging ("HL7 orders").

A third class of data is known as "diagnoses." Diagnoses may be included within modules within an EHR. Diagnoses may be indicated via diagnostic codes. For example, a diagnosis may include an ICD 10 code that starts with "E11%"—Diabetes diagnoses, a Human immunodeficiency virus [HIV] disease B20 code, etc. This class of information may be analyzed by searching for a specific alphanumeric code associated with the diagnosis in order to trigger a clinical notification, or may be analyzed by searching for textual descriptions of the diagnosis. Diagnoses may be harvested from HL7 DG1 messaging.

A fourth category of data is "allergies." These may be further categorized by type, such as "medication" and "environmental." Examples of allergies include latex allergies, specific antibiotics, other medications, etc. This class of information may be analyzed by searching for textual descriptions of the allergies, or specific codes indicating the allergies. These allergies may be indicated in HL7 CDA messages or in Admissions messages A01, A04, A08 in the AL1 segment.

A fifth category of data is DNR status, which may be obtained from an ADT feed. Example values for DNR status are true or false. DNR status may be indicated in HL7 A01, A04, or A08 admissions messages. A sixth category of data is opt out status, which may also be obtained from an ADT feed. Updates from subsequent HL7 messaging (e.g., A01, A04, A08) may update the opt out status with more recent data, for example in order to inactivate the notification. Opt out status may be indicated as true or false, and may further be indicated in HL7 A01, A04, or A08 messages.

A seventh category of data is Very Important Person (VIP) status, which may be obtained via an ADT feed, as well as A01, A04, or A08 messages. An eighth category of data is demographics, which include for example age, Date of Birth (DOB), address, ZIP code, etc. demographics may be obtained via an ADT feed, as well as A01, A04, or A08 messages.

Figure 8:
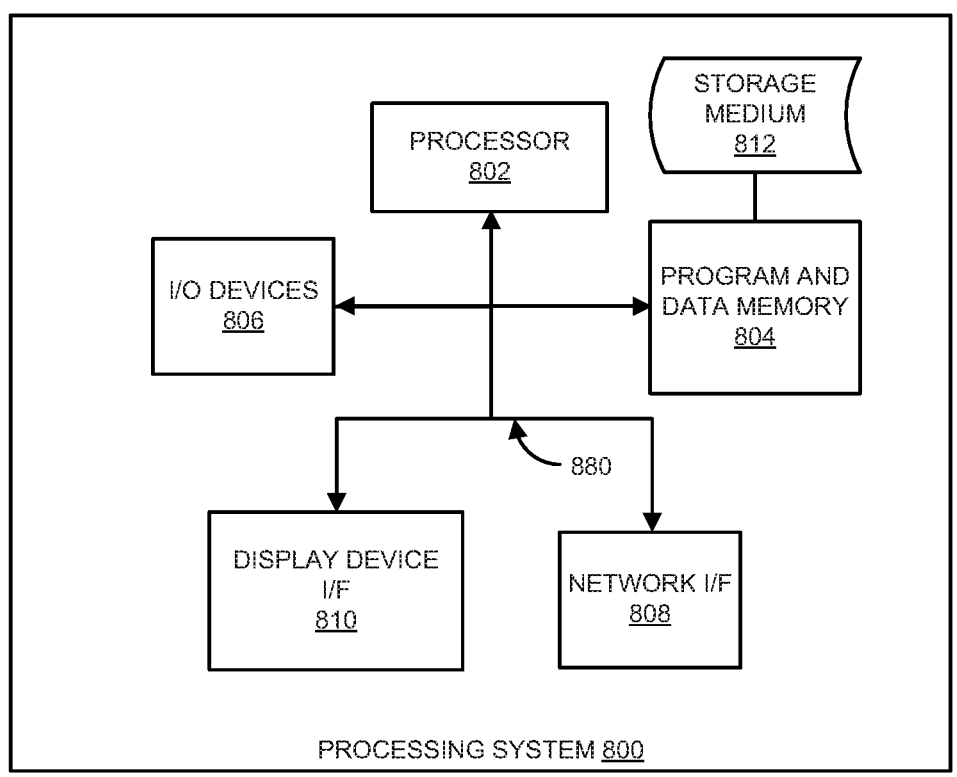
FIG. 8 illustrates a processing system operable to execute a computer readable medium embodying programmed instructions to perform desired functions in an exemplary embodiment.

Embodiments disclosed herein can take the form of software, hardware, firmware, or various combinations thereof. In one particular embodiment, software is used to direct a processing system of labeling server 150 to perform the various operations disclosed herein. FIG. 8 illustrates a processing system 800 operable to execute a computer readable medium embodying programmed instructions to perform desired functions in an exemplary embodiment. Processing system 800 is operable to perform the above operations by executing programmed instructions tangibly embodied on computer readable storage medium 812. In this regard, embodiments of the invention can take the form of a computer program accessible via computer-readable medium 812 providing program code for use by a computer or any other instruction execution system. For the purposes of this description, computer readable storage medium 812 can be anything that can contain or store the program for use by the computer.

Computer readable storage medium 812 can be an electronic, magnetic, optical, electromagnetic, infrared, or semiconductor device. Examples of computer readable storage medium 812 include a solid state memory, a magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-R/W), and DVD.

Processing system 800, being suitable for storing and/or executing the program code, includes at least one processor 802 coupled to program and data memory 804 through a system bus 850. Program and data memory 804 can include local memory employed during actual execution of the program code, bulk storage, and cache memories that provide temporary storage of at least some program code and/or data in order to reduce the number of times the code and/or data are retrieved from bulk storage during execution.

Input/output or I/O devices 806 (including but not limited to keyboards, displays, pointing devices, etc.) can be coupled either directly or through intervening I/O controllers. Network adapter interfaces 808 may also be integrated with the system to enable processing system 800 to become coupled to other data processing systems or storage devices through intervening private or public networks. Modems, cable modems, IBM Channel attachments, SCSI, Fibre Channel, and Ethernet cards are just a few of the currently available types of network or host interface adapters. Display device interface 810 may be integrated with the system to interface to one or more display devices, such as printing systems and screens for presentation of data generated by processor 802.

Although specific embodiments were described herein, the scope of the invention is not limited to those specific embodiments. The scope of the invention is defined by the following claims and any equivalents thereof.

What is claimed is:

1. A system comprising:
a labeling system comprising:
an interface;
a memory storing rules that indicate on a patient-by-patient basis whether to print clinical notifications onto wearable patient identifiers, based on fields of electronic health records acquired via Health Level 7 (HL7) messaging; and
a controller that presents a Graphical User Interface (GUI) that includes interactive elements that enable alteration of the rules, the interactive elements comprising, for each of multiple rules that each pertain to a separate clinical notification:
a first dialogue that indicates a field storing data to acquire from an electronic health record, and is operable by a user to select from among multiple fields in the electronic health record;
a second dialogue that indicates a value to compare to the data, and is operable by a user to select from among multiple values; and
an operator that logically combines the data and the value to arrive at a Boolean result, and is operable to be replaced by a user with a different operator via the GUI;
wherein the GUI further includes interactive elements that enable the addition of new rules and deletion of existing rules, wherein in response to adding a new rule, the GUI displays an additional first dialogue, second dialogue, and operator pertaining to the new rule without removing dialogues and operators for other rules, such that the GUI enables simultaneous editing of the rules, and
for each rule, the controller determines whether to include a clinical notification in print data for a wearable patient identifier, based on the Boolean result.

2. The system of claim 1 wherein:
the controller detects modifications to the dialogues, and updates the rules stored in the memory based on the modifications.

3. The system of claim 2 wherein:
in response to detecting a modification to the first dialogue, the controller alters which field of the electronic health record is accessed when acquiring the data.

4. The system of claim 2 wherein:
in response to detecting a modification to the second dialogue, the controller alters the value that the data is compared to.

5. The system of claim 2 wherein:
in response to detecting a modification to the operator, the controller alters how the data and the value are logically combined.

6. The system of claim 1 wherein:
the first dialogue, the second dialogue, and the operator define a first logical condition; and
the interactive elements for at least one rule include multiple logical conditions.

7. The system of claim 1 wherein:
the first dialogue indicates a field by name.

8. A method comprising:
storing rules that indicate on a patient-by-patient basis whether to print clinical notifications onto wearable patient identifiers, based on fields of electronic health records acquired via Health Level 7 (HL7) messaging; and
directing a display to present a Graphical User Interface (GUI) that includes interactive elements that enable alteration of the rules, the interactive elements comprising, for each of multiple rules that each pertain to a separate clinical notification:
a first dialogue that indicates a field storing data to acquire from an electronic health record, and is operable by a user to select from among multiple fields in the electronic health record;
a second dialogue that indicates a value to compare to the data, and is operable by a user to select from among multiple values; and
an operator that logically combines the data and the value to arrive at a Boolean result, and is operable to be replaced by a user with a different operator via the GUI;
wherein the GUI further includes interactive elements that enable the addition of new rules and deletion of existing rules, wherein in response to adding a new rule, the GUI displays an additional first dialogue, second dialogue, and operator pertaining to the new rule without removing dialogues and operators for other rules, such that the GUI enables simultaneous editing of the rules, and the method further comprises:
determining whether to include a clinical notification in print data for a wearable patient identifier, based on the Boolean result.

9. The method of claim 8 further comprising:
detecting modifications to the dialogues; and
updating the rules stored in the memory based on the modifications.

10. The method of claim 9 further comprising:
in response to detecting a modification to the first dialogue, altering which field of the electronic health record is accessed when acquiring the data.

11. The method of claim 9 further comprising:
in response to detecting a modification to the second dialogue, altering the value that the data is compared to.

12. The method of claim 9 further comprising:
in response to detecting a modification to the operator, altering how the data and the value are logically combined.

13. The method of claim 8 wherein:
the first dialogue, the second dialogue, and the operator define a first logical condition; and
the interactive elements for at least one rule include multiple logical conditions.

14. The method of claim 8 wherein:
the first dialogue indicates the field by name.

15. A non-transitory computer readable medium embodying programmed instructions which, when executed by a processor, are operable for performing a method comprising:
storing rules that indicate on a patient-by-patient basis whether to print clinical notifications onto wearable patient identifiers, based on fields of electronic health records acquired via Health Level 7 (HL7) messaging; and
directing a display to present a Graphical User Interface (GUI) that includes interactive elements that enable alteration of the rules, the interactive elements comprising, for each of multiple rules that each pertain to a separate clinical notification:
a first dialogue that indicates a field storing data to acquire from an electronic health record, and is operable by a user to select from among multiple fields in the electronic health record;
a second dialogue that indicates a value to compare to the data, and is operable by a user to select from among multiple values; and
an operator that logically combines the data and the value to arrive at a Boolean result, and is operable to be replaced by a user with a different operator via the GUI;
wherein the GUI further includes interactive elements that enable the addition of new rules and deletion of existing rules, wherein in response to adding a new rule, the GUI displays an additional first dialogue, second dialogue, and operator pertaining to the new rule without removing dialogues and operators for other rules, such that the GUI enables simultaneous editing of the rules, and the method further comprises:
determining whether to include a clinical notification in print data for a wearable patient identifier, based on the Boolean result.

16. The medium of claim 15 wherein the method further comprises:
detecting modifications to the interactive elements; and
updating the rules stored in the memory based on the detected modifications.

17. The medium of claim 15 wherein the method further comprises:
in response to detecting a modification to the first dialogue, altering which field of the electronic health record is accessed when acquiring the data.

18. The medium of claim 15 wherein the method further comprises:
in response to detecting a modification to the second dialogue, altering the value that the data is compared to.

19. The medium of claim 15 wherein the method further comprises:
in response to detecting a modification to the operator, altering how the data and the value are logically combined.

20. The medium of claim 15 wherein:
the first dialogue, the second dialogue, and the operator define a first logical condition; and
the interactive elements for at least one rule include multiple logical conditions.

\* \* \* \* \*